(12) United States Patent
Lemaire et al.

(10) Patent No.: US 11,376,296 B2
(45) Date of Patent: Jul. 5, 2022

(54) **COSMETIC COMPOSITION COMPRISING AN ESSENTIAL OIL OF IMMORTELLE AND AN EXTRACT OF *ORIGANUM***

(71) Applicant: LABORATOIRES M&L, Manosque (FR)

(72) Inventors: Géraldine Lemaire, Valensole (FR); Valérie Cenizo, Meyrargues (FR); Cédric Khan, Pierrevert (FR); Pascal Portes, Puyricard (FR)

(73) Assignee: LABORATOIRES M&L, Manosque (FR)

( * ) Notice: Subject to any disclaimer, the term of this patent is extended or adjusted under 35 U.S.C. 154(b) by 0 days.

(21) Appl. No.: 16/626,586

(22) PCT Filed: Jun. 14, 2018

(86) PCT No.: PCT/FR2018/051412
§ 371 (c)(1),
(2) Date: Dec. 26, 2019

(87) PCT Pub. No.: WO2019/002714
PCT Pub. Date: Jan. 3, 2019

(65) Prior Publication Data
US 2020/0113959 A1    Apr. 16, 2020

(30) Foreign Application Priority Data
Jun. 29, 2017 (FR) .................................... 1756021

(51) Int. Cl.
*A61K 36/28* (2006.01)
*A61K 8/92* (2006.01)
*A61K 36/53* (2006.01)
*A61Q 19/00* (2006.01)
*A61Q 19/08* (2006.01)

(52) U.S. Cl.
CPC .............. *A61K 36/28* (2013.01); *A61K 8/922* (2013.01); *A61K 36/53* (2013.01); *A61Q 19/007* (2013.01); *A61Q 19/08* (2013.01); *A61K 2800/591* (2013.01)

(58) Field of Classification Search
None
See application file for complete search history.

(56) References Cited

U.S. PATENT DOCUMENTS

| 9,040,066 B2 * | 5/2015 | Beeson ................. A61K 8/676 424/401 |
| 2004/0258783 A1 | 12/2004 | Millou et al. |
| 2007/0141019 A1 | 6/2007 | Long |
| 2016/0346191 A1 | 12/2016 | Petkoska et al. |

FOREIGN PATENT DOCUMENTS

| FR | 2 999 926 | 6/2014 |
| JP | 2007-016077 | 1/2007 |
| JP | 2011-236149 | 11/2011 |
| WO | WO 03/018730 | 3/2003 |
| WO | WO 2012/153064 | 11/2012 |
| WO | WO 2017/077232 | 5/2017 |

OTHER PUBLICATIONS

Raskin et al. (2004) Current Pharmaceutical Design 10: 3419-3429. (Year: 2004).*
Revilla et al. (1998) J. Agric. Food Chem. 46: 4592-4597. (Year: 1998).*
Tallarida (2011) Genes and Cancer 2(11): 1003-1008. (Year: 2011).*
Written Opinion in International Application No. PCT/FR2018/051412, dated Oct. 23, 2018, pp. 1-10.

* cited by examiner

*Primary Examiner* — Russell G Fiebig
(74) *Attorney, Agent, or Firm* — Saliwanchik, Lloyd & Eisenschenk

(57) ABSTRACT

The present invention relates to a cosmetic composition containing an essential oil of Immortelle and a terpene extract of at least one plant of the *Origanum* genus, in particular of *Origanum majorana*, and also to the cosmetic use thereof in skincare, in particular for combating the signs of aging on the skin and/or dryness skin.

2 Claims, No Drawings

COSMETIC COMPOSITION COMPRISING AN ESSENTIAL OIL OF IMMORTELLE AND AN EXTRACT OF *ORIGANUM*

CROSS-REFERENCE TO RELATED APPLICATION

This application is the U.S. national stage application of International Patent Application No. PCT/FR2018/051412, filed Jun. 14, 2018.

SUBJECT OF THE INVENTION

The present invention relates to a cosmetic composition containing an essential oil of Immortelle and a terpene extract of at least one plant of the *Origanum* genus, in particular *Origanum majorana*, and also to the cosmetic use thereof for skincare, in particular for combating the signs of aging on the skin and/or dry skin.

BACKGROUND OF THE INVENTION

Skin aging is determined by genetic and environmental factors. A distinction is usually made between intrinsic aging, or chronological aging, which affects the skin, as it does the other organs, and corresponds to the inevitable modifications related to age, and extrinsic aging which is linked to environmental factors and in particular to characteristic clinical, histological and functional modifications of the skin related to chronic exposure to the sun and which thus are located on photo-exposed areas.

These two processes are closely linked and, in both cases, the production of reactive oxygen species (ROSs), resulting in oxidative stress, is a determining element in skin aging. It is defined as an excess of free radicals present in the organism resulting from an excessive production by various physiological mechanisms or from exogenous toxic phenomena (such as smoking, pollution, blue light or UV exposure). These reactive oxygen species (ROSs) and free radicals can thus be generated either by the cell metabolism, such as mitochondrial respiration, or else by detoxification of xenobiotics or solar radiation.

In principle, this physiological production of free radicals is controlled by cell defense systems. However, said systems are affected by various factors, such as a deficiency in antioxidants or a decrease in antioxidant enzyme activity, or else by the overproduction of reactive oxygen species, thus resulting in a disequilibrium of the antioxidant/pro-oxidant defense balance and thus in a state of oxidative stress. It is widely accepted that this oxidative stress plays a significant role in skin aging. In particular, the degradation of lipids and proteins in the skin under the effect of oxidative stress leads to slackening of the skin, the formation of wrinkles and pigment spots and a loss of elasticity of the skin and of radiance of the complexion. It has also been observed that nitrogen monoxide produced in excess when there is a disequilibrium of the redox balance inhibits the synthesis of proteins required for cornification of the epidermis and thus destructs the barrier function.

Other phenomena lead to a destruction of the barrier function, and in particular the reduction, linked to aging, of the renewal and differentiation capacity of keratinocytes. The impairment of the epidermal barrier results in dehydration of the epidermis and in turn leads to a greater permeability of the skin to oxidizing and polluting agents.

The advantage of having means for reinforcing the skin barrier and protecting skin against oxidative stress is thus understood.

The applicant has already proposed using an essential oil of Immortelle, rich in terpene compounds, as an anti-aging agent, because of its free-radical scavenging and moisturizing properties (WO 03/018730), or for reinforcing the barrier function (WO 2012/153064).

Among the other plants of the Mediterranean basin that have been described as effective against oxidative stress, mention may be made of polyphenols (EP 3 069 710) or carnosic acid (U.S. Pat. No. 9,040,066) derived from marjolaine or *Origanum majorana*. Other marjolaine extracts are also known as anti-aging active agents. Thus, the company BASF sells, under the tradename Dermagenist®, an aqueous extract of marjolaine rich in terpenes, for its DNA methylation-inhibiting properties. It is thus suggested that this extract could be of use for stimulating the formation of elastic fibers which degrade with age and under the effect of UV exposure (FR 2 999 926).

However, there remains the need to provide a cosmetic composition which makes it possible to effectively combat the signs of skin aging and in particular to reinforce the skin barrier and the response of the skin to oxidative stress.

SUMMARY OF THE INVENTION

The applicant has demonstrated that the combination of a terpene extract of *Origanum* with an essential oil of Immortelle synergistically activates the Nrf2 pathway which is known to be linked to the response to oxidative stress. The Nrf2 transcription factor is in fact a powerful transcription activator which plays a central role in the inducible expression of numerous cytoprotective genes in response to oxidative and electrophilic stress. The target genes of Nrf2 are in particular involved in glutathione synthesis, reactive oxygen species elimination and cell detoxification enzymes. The applicant has also demonstrated an increase, which is also synergistic, in the expression of the genes involved in the epidermal differentiation process by means of the combination of a terpene extract of *Origanum* with an essential oil of Immortelle. It thus appeared to the applicant that the abovementioned combination made it possible to formulate a cosmetic composition that is efficacious against the signs of skin aging and/or dryness of the skin.

In this context, a subject of the invention is a cosmetic composition comprising an essential oil of Immortelle and a terpene extract of at least one plant of the *Origanum* genus.

Another subject of the invention is the use of the abovementioned composition for combating the signs of skin aging, in particular the formation of wrinkles, the slackening of the skin and the loss of radiance of the complexion, caused in particular by exposure to blue light, to UV radiation, to smoking and/or to pollution and/or for combating dryness of the skin.

Another subject of the invention is a cosmetic process for combating the signs of skin aging, in particular the formation of wrinkles, the slackening of the skin and the loss of radiance of the complexion, caused in particular by exposure to blue light, to UV radiation, to smoking and/or to pollution, and/or for combating dryness of the skin, comprising the topical application of the abovementioned composition to the skin.

DETAILED DESCRIPTION

The present invention uses an essential oil of Immortelle. Among the species of Immortelle that may be used according to the invention mention will be made of all those which are from the *Helichrysum* genus and in particular *Helichrysum italicum* (or *Helichrysum angustifolium* D.C), which is the curry plant, *Helichrysum arenarium*, which is sandy everlasting, and *Helichrysum stoechas* or common everlasting flower, without this list being limiting. An essential oil of *Helichrysum italicum* is preferentially used, regardless of the subspecies in question.

In this description, the term "essential oil" is intended to mean the product of hydrodistillation or of steam stripping of the volatile organic compounds present in any part of the Immortelle or the whole plant, and more particularly in its aerial parts, such as for example its flowers or flowering heads.

The essential oil of Immortelle advantageously represents from 0.001 to 5% by weight and preferentially from 0.001 to 0.1% by weight, relative to the total weight of the composition according to the invention.

In this composition, it is combined with a terpene extract of at least one plant of the *Origanum* genus, in particular of the species *Origanum vulgare* and *Origanum majorana*. Preferably, the plant of the *Origanum* genus belongs to the species *Origanum majorana*.

Use may be made of an extract obtained from all or part of the plant of the *Origanum* genus, in particular the root, the stem, the bark, the flower, the seed, the germ and/or the leaf and preferentially from the aerial plants chosen from the stem, the leaves and mixtures thereof, preferentially the leaves.

The extract can be obtained by any process suitable for the extraction of a predominant weight fraction of terpene compounds and in particular by extraction using a protic polar solvent comprising, preferably consisting of, at least one solvent chosen from water, a monoalcohol (such as ethanol or isopropanol), a glycol (such as propylene glycol or butylene glycol), a polyol (such as xylitol) and mixtures thereof. The extraction can be carried out under cold conditions (maceration) or under hot conditions, preferably at a temperature of 4 to 20° C. The amount of plant used can represent from 1 to 10% by weight, relative to the weight of solvent(s). The extraction step is generally followed by a step of separation of the solids and of the supernatant, for example by centrifugation, of recovery of the supernatant, in particular by filtration, and optionally of distillation. The extract obtained can optionally be dried by spray-drying and/or freeze-drying. Steps of deodorizing and/or decoloring the extract can be carried out after extraction, at any stage of the process described above.

Such an extract of *Origanum majorana* is in particular available from the company BASF under the tradename Dermagenist®.

The extract of *Origanum* advantageously represents from 0.001 to 5% by weight and preferentially from 0.01 to 0.4% by weight, relative to the total weight of the composition according to the invention.

As emerges from the examples below, it has been demonstrated that the combination of plant extracts according to the invention makes it possible to synergistically activate the expression of the genes involved in the defense of the skin against oxidation phenomena, and of the genes involved in the regulation of epidermal differentiation.

In the context of this description, the term "synergy" is intended to mean that the effect obtained using the combination of extracts according to the invention is significantly greater than the effect obtained using either one of the two extracts.

The above combination is included in a cosmetic composition which generally contains a physiologically acceptable medium, in particular a cosmetically acceptable medium, that is to say which does not generate tingling or redness incompatible with cosmetic use. This medium preferably contains an aqueous phase (containing for example the extract of *Origanum*) and a fatty phase (generally containing the essential oil of Immortelle). The composition is preferably in the form of an oil-in-water or water-in-oil emulsion or of an oil-in-water dispersion.

The aqueous phase contains water and optionally at least one constituent chosen from polyols and aqueous gelling agents. The water advantageously represents from 40 to 80%, preferably from 60 to 70%, of the total weight of the composition. The polyol may in particular be chosen from glycerol, propylene glycol, butylene glycol, pentylene glycol and mixtures thereof and it may represent from 5 to 30%, preferably from 15 to 25%, of the total weight of the composition.

The term "aqueous gelling agent" denotes a polymeric compound capable of immobilizing water molecules by hydrating and of thus increasing the viscosity of the aqueous phase. Such a gelling agent can be chosen from, polysaccharides, such as: cellulose and derivatives thereof, modified starches, carrageenan, agar agar, xanthan gum and plant gums such as guar gum or locus beam gum; synthetic polymers and in particular optionally crosslinked sodium acrylate homopolymers, and also acrylic copolymers, in particular copolymers of sodium acrylate and/or alkyl (meth)acrylate and/or of hydroxylalkyl (meth)acrylate and/or (polyethoxy)alkyl (meth)acrylate, optionally with at least one other monomer, advantageously 2-acrylamido-2-methylpropanesulfonic acid (AMPS), these polymers being optionally crosslinked; and mixtures thereof.

For its part, the fatty phase may comprise one or more volatile and/or nonvolatile oils. Examples of volatile oils are branched $C_{10}$-$C_{13}$ alkanes, such as isododecane, and linear $C_{10}$-$C_{13}$ alkanes. As nonvolatile oils, mention may in particular be made of:

esters of acids and of monoalcohol, chosen from: mono- and polyesters of saturated linear $C_2$-$C_{10}$ (preferably $C_6$-$C_{10}$) acids and of saturated linear $C_{10}$-$C_{18}$ (preferably $C_{10}$-$C_{14}$) monoalcohols, mono- and polyesters of saturated linear $C_{10}$-$C_{20}$ acids and of branched or unsaturated $C_3$-$C_{20}$ (preferably $C_3$-$C_{10}$) monoalcohols; mono- and polyesters of branched or unsaturated $C_5$-$C_{20}$ acids and of branched or unsaturated $C_5$-$C_{20}$ monoalcohols; mono- and polyesters of branched or unsaturated $C_5$-$C_{20}$ acids and of linear $C_2$-$C_4$ monoalcohols;

$C_6$-$C_{12}$ fatty acid triglycerides, such as caprylic and capric acid triglycerides and triheptanoin;

branched and/or unsaturated $C_{10}$-$C_{20}$ fatty acids (such as linoleic, lauric and myristic acids);

branched and/or unsaturated $C_{10}$-$C_{20}$ fatty alcohols (such as octyldodecanol and oleyl alcohol);

hydrocarbons such as squalane ($C_{30}$), in particular plant squalane extracted from olive oil, and hemisqualane ($C_{15}$);

dialkyl carbonates, such as dicaprylyl carbonate and diethylhexyl carbonate;

dialkyl ethers such as dicaprylyl ether; and mixtures thereof.

Mention may also be made of plant oils which contain one or more of the abovementioned constituents.

As esters of acids and of monoalcohols, mention may in particular be made of monoesters such as the mixture of coco caprate and caprylate, ethyl macadamiate, shea butter ethyl ester, isostearyl isostearate, isononyl isononanoate, ethylhexyl isononanoate, hexyl neopentanoate, ethylhexyl neopentanoate, isostearyl neopentanoate, isodecyl neopentanoate, isopropyl myristate, octyldodecyl myristate, isopropyl palmitate, ethylhexyl palmitate, hexyl laurate, isoamyl laurate, cetostearyl nonanoate, propylheptyl caprylate, and mixtures thereof. Other esters that may be used are diesters of acids and of monoalcohols such as diisopropyl adipate, diethylhexyl adipate, diisopropyl sebacate and diisoamyl sebacate.

Examples of plant oils are in particular wheat germ, sunflower, argan, hibiscus, coriander, grapeseed, sesame, corn, apricot, castor, shea, avocado, olive and soybean oils, sweet almond oil, and palm, rapeseed, cottonseed, hazelnut, macadamia, jojoba, alfalfa, poppy, pumpkin, sesame, marrow, blackcurrant, evening primrose, lavender, borage, millet, barley, quinoa, rye, safflower, candlenut, passion flower, musk rose, Echium, camelina or camelia oil.

The fatty phase may also comprise at least one fatty-phase structuring agent. The term "fatty-phase structuring agent" is intended to mean a compound capable of thickening the oils contained in the composition, chosen in particular from waxes, fatty-phase gelling agents, and pasty fatty substances, and also mixtures thereof.

According to one preferred embodiment, this composition also contains at least one anti-aging active agent, in particular an active agent suitable for preventing and/or treating wrinkles, slackening of the skin and/or the formation of pigment spots, which can in particular be chosen from free-radical scavengers, agents which stimulate keratinocyte and/or fibroblast differentiation and/or proliferation; agents which stimulate the synthesis of glycosaminoglycans and/or of collagen and/or of dermoepidermal anchoring fibrils and/or elastic fibers; agents which prevent the degradation of collagen and/or of glycosaminoglycans and/or of dermoepidermal anchoring fibrils and/or elastic fibers; anti-glycation agents; depigmenting and/or melanogenesis-inhibiting agents; and mixtures thereof.

Examples of such anti-aging active agents are in particular: ascorbic acid, salts thereof, ethers thereof and esters thereof, in particular ascorbyl glucoside; adenosine; ribose; honey extracts; proteins and glycoproteins, extracted in particular from sweet almond; hydrolyzed plant proteins, in particular from rice, from hibiscus seeds or from lupin; polypeptides and pseudodipeptides, such as carcinine hydrochloride, the palmitoyl pentapeptide-4 (Pal-Lys-Thr-Thr-Lys-Ser) and the palmitoyl tripeptide-38 sold in particular by Sederma under the trade names Matrixyl® 3000 and Matrixyl® Synthe'6, respectively, the palmitoyl tripeptide-8 sold by the company Lucas Meyer under the trade reference Nutrazen®, the pentapeptide-18 sold by the company Lipotec under the trade name Leuphasyl® Solution, the sh-decapeptide-9 sold by the company Sandream under the trade name Neoendorphin® and the palmitoyl hexapeptide-52 sold by the company Infinitec under the trade reference X50 Myocept® Powder; silanes, such as methylsilanol mannuronate; arabinoxylans, extracted in particular from rye flour, and galactoarabinans, in particular from larch; hyaluronic acid and salts thereof; polyphenols, extracted in particular from *mimosa*; alpha-hydroxy acids, including those extracted from lemon; (generally aqueous extracts) of plants such as buckbean, wild pansy, field horsetail, paracress (*Acmella oleracea*), Scottish thistle (*Onopordum acanthium*), yarrow (*Achillea millefolium*, contained in particular in the product Neurobiox® from the company BASF), embelia (*Embelia concinna*, as sold by the company SEPPIC), Barbary fig (*Opuntia ficus* indica, sold in particular by Mibelle AG Biochemistry under the tradename Aqua-Cacteen®), sage (*Salvia officinalis*, sold in particular by Provital Group), *Vitex negundo* (sold in particular by Laboratoires Expanscience under the trade reference Neurovity®), sweet chestnut, daisy, argan tree, oat, sunflower, daisy, peony or dill; aqueous extracts of algae and in particular of coralline algae, of *Jania rubens*, of *Ungaria pinnatifada*, of *Alaria esculenta* or of *Nannochlorosis oculata*; essential oils, in particular of myrtle; zinc gluconate and/or copper gluconate; and mixtures thereof.

As a variant or in addition, the composition used according to the invention may comprise at least one tensioning agent. It may be a tensioning polymer, capable of tensioning the skin by mechanical action and of thus reducing the appearance of wrinkles and fine lines, in particular a polysaccharide, especially an extract of algae or of marine plankton or of a plant gum. It may also be a tensioning agent which acts biologically, of the botox-like type, for example an extract of *Acmella oleracea* sold under the name Gatuline® Expression by the company Gattefosse; an extract of hibiscus seeds sold under the name Myoxinol® LS9736 by the company BASF BCS or else a peptide of acetyl hexapeptide-8 type sold under the name Argireline® by the company Lipotec.

The composition according to the invention may also contain various constituents which can be dispersed in the fatty phase and/or in the aqueous phase of the emulsion, provided that they are compatible with topical application to the skin.

It may thus contain at least one generally nonionic oil-in-water or water-in-oil emulsifier, such as polyoxyethylene esters, optionally polyethoxylated sorbitan esters, optionally polyethoxylated esters of fatty acids and of glycerol, ethers of fatty alcohols and of sugar, such as alkyl glucosides, and mixtures thereof. The emulsifiers may represent from 2 to 10% and preferably from 4 to 6% of the total weight of the composition. However, the composition according to the invention is preferably free of emulsifier.

The composition according to the invention may also comprise one or more pulverulent fillers, which are advantageously in the form of porous or hollow, preferably porous, microparticles. These microparticles are in principle substantially spherical. These fillers can in particular be chosen from:

organic fillers such as: polysaccharide powders and in particular native starch powders, modified starch powders or cellulose powders; powders of acrylic polymers such as poly(methyl methacrylate) of polyamides or of polyolefins; powders of dried algae such as *Corallina officinalis;* inorganic fillers such as silica, clays, perlite and talc; and mixtures thereof.

Silica is preferably used as inorganic filler.

These fillers can represent from 1 to 5% by weight, relative to the total weight of the composition.

The composition according to the invention can also comprise additives chosen in particular from organic and/or inorganic photoprotective agents, agents that are active in blue light and/or UVA and/or UVB; polysaccharide-based film-forming polymers capable of forming an anti-pollution protective film, such as the product sold by Solabia under the tradenames Pollustop® and Solashield®; desquamanting agents such as α- and β-hydroxy acids; exfoliant particles; fragrances; antioxidants; sequestering agents; pH adjusters, preserving agents; pigments; dyes; and mixtures thereof.

This composition can be in any form suitable for topical application to the skin and in particular in milk, cream, lotion, gel, paste or film form. The composition is generally a leave-on composition and in particular a care composition, a makeup composition, such as a foundation, or an antisun composition.

The composition according to the invention can be applied to at least one area of the body of an individual exhibiting signs of skin aging (for example at least 30 years old, or even at least 40 years old), and more particularly to the face, the neck and/or the neckline. As a variant, it can be applied to all of the body, in particular to the chest, the arms, the legs and the stomach for the purpose of combating drying out of the skin.

This composition can be applied one or more times a day, for example in the morning and/or in the evening, to the areas to be treated.

As a variant, the composition according to the invention may be a rinse-off composition used for caring for the skin, in particular of the face and optionally of the body. In this case, it can for example be used as a scrubbing paste or mask.

EXAMPLES

The invention will be understood more clearly in the light of the following examples, which are given purely by way of illustration and are not intended to limit the scope of the invention, defined by the appended claims.

Example 1: Ex-Vivo Test on Human Skin Explant

A transcriptome analysis was carried out in order to demonstrate the effect of the combination of plants according to the invention on the expression of certain genes in the skin.

The transcriptome is the set of messenger RNAs resulting from the expression of a portion of the genome in a given tissue or cell type. The characterization and quantification of the transcriptome make it possible to identify the genes regulated under particular conditions, to determine the mechanisms for regulating these genes and to define the networks of expression or pathways for activation of these genes. One of the techniques used to simultaneously measure the expression level of a large number of different messenger RNAs is DNA chip technology. DNA chips make it possible to very rapidly measure and visualize the differences in expression on the scale of a complete genome.

1) MATERIALS AND METHODS

Sample Preparation

An aqueous extract of marjolaine (*Origanum majorana*) leaves, an essential oil of Immortelle (*Helichrysum italicum*), obtained by hydrodistillation, or the combination of the two extracts, were placed in the presence of skin explants under survival conditions. The essential oil of Immortelle was solubilized at 10% in dimethyl sulfoxide (DMSO) before being applied in the culture medium. The marjolaine extract was directly diluted in the culture medium.

4 skin explants originating from an abdominoplasty of a 34-year-old patient were independently incubated, in the presence of the marjolaine extract, of the essential oil of Immortelle or of the combination thereof for 24 h in a "skin culture medium" from the company Biopredic at 37° C. at 5% $CO_2$ in a humid atmosphere (98%) at the air-liquid interface. 4 skin explants that were not treated or treated with the DMSO solvent at 1% were incubated under the same conditions.

Table 1 below summarizes the concentrations applied for each composition.

TABLE 1

| Composition | Percentage (%) |
| --- | --- |
| Marjolaine extract | 0.4 |
| Essential oil of Immortelle | 0.1 |
| Marjolaine extract and | 0.4 |
| essential oil of Immortelle | 0.1 |

Total RNA Extraction

After incubation, the skin explants were ground in the buffer recommended by the producer of the RNeasy RNA extraction mini kit (Qiagen, Hilden, Germany) then the total RNAs were extracted using this same kit. The total RNAs were quantified and then their quality was verified using the BIOanalyzer 2100 electrophoresis instrument with its RNA 6000 Nano LabChip Kit analysis kit (Agilent Technologies, Santa Clara, USA).

Measurement of the Gene Expression on an Oligonucleotide Chip and Data Acquisition:

Oligonucleotide chips of 60mers on 1"×3" glass coverslips (SurePrint G3 Human Gene Expression 8×60K v2 Microarray-G4851B, Agilent Technologies, Santa Clara, USA) were used for the gene expression analysis.

Documentation and also the complete experimental protocol are available on the Agilent Technologies website.

Briefly, reverse transcription and amplification of the total RNAs into cDNAs and then into cRNAs and the labeling thereof with cyanine 3 are carried out using the Low Input Quick Amp Labeling kit (Agilent Technologies). The cRNAs were purified using the RNeasy mini kit (Qiagen, Hilden, Germany) and hybridization was carried out with the Microarray hybridization chamber kit (Agilent Technologies, Santa Clara, USA). The chips were then scanned using the SureScan scanner (Agilent Technologies, Santa Clara, USA) and the Scan control software (Agilent Technologies, Santa Clara, USA). The scanned images were then extracted and standardized with the Feature Extraction software (Agilent Technologies, Santa Clara, USA).

The statistical analysis of the data was carried out using the Genespring GX 13 software (Agilent Technologies, Santa Clara, USA).

The Ingenuity Pathways Analysis software (Ingenuity® Pathway Analysis (IPA), Ingenuity Systems, Redwood City, Calif., USA, see Worldwide Website: ingenuity.com) was then used to analyze and predict the state of activation of the biological pathways modulated by the marjolaine extract, the essential oil of Immortelle or a combination thereof.

For each treatment condition, 4 independent labeling experiments were carried out (that is to say 4 oligonucleotide chips per condition, corresponding to the 4 skin explants treated independently for each condition) in order to increase the data reproducibility.

The genes expressed by the treated skin explants were considered to be induced or inhibited if their differential expression level was greater by a factor of 2 compared with those of the controlled explants. The nontreated explants served as a control for the condition treated with the marjolaine extract and the explants treated with the DMSO solvent at 1% served as a control for the condition treated with the essential oil of Immortelle or the combination of the marjolaine extract and the essential oil of Immortelle. A moderated Student's test corrected for the false positive rate was applied with the procedure of Benjamini & Hochberg by means of the GeneSpring software in order to calculate the statistical difference in gene expression with the explants that were not treated or were treated with the DMSO solvent and the explants that were treated with the active agents or a combination thereof. The genes of which the p value was less than or equal to 0.05 were considered to be differentially expressed.

These genes were then analyzed using the Ingenuity Pathways Analysis software. This software allows a functional analysis of the genes regulated under the various treatment conditions, an analysis of the signaling pathways in which these genes lie and the analysis of the regulators upstream of these pathways. A Z-score (reduced centered variable) was calculated by the software with respect to the significantly regulated genes. A Z-score>2 or <−2 indicates a confidence interval of 99% that the biological pathways induced or suppressed are not done so only by chance, but very specifically.

2) Results

2a) Antioxidant Defenses: Activation of the Nrf2 Pathway

The table below presents the difference in expression of the genes that are involved in the Nrf2 pathway of antioxidant defense following the treatment of the skin explants with the marjolaine extract, the essential oil of Immortelle and a combination thereof.

| GENES | | | Expression with respect to the nontreated control or to the solvent control | | |
|---|---|---|---|---|---|
| Symbol | English name | Function of the protein encoded by the gene | Marjolaine | Ess. O Immortelle | Marjolaine and Ess. O Immortelle |
| ABCC1 | ATP binding cassette subfamily C member 1 | Allows transport of the reduced and oxidized forms of glutathione through the plasma membrane and plays a role in the protection against xenobiotics | | | 2.566 |
| ACTA1 | actin, alpha 1, skeletal muscle | Structural proteins | | 9.406 | 11.417 |
| ACTB | actin beta | | | | 2.025 |
| ATF4 | activating transcription factor 4 | Protein which interacts with Nrf2 (cofactor) | | 2.316 | 2.671 |
| CDC34 | cell division cycle 34 | Belongs to the family of enzymes for conjugation of ubiquitin involved in the proteasome pathway and protein repair | | | 2.376 |
| DNAJA1 | DnaJ heat shock protein family (Hsp40) member A1 | Chaperone proteins which protect against oxidative stress | | | 2.029 |
| DNAJB1 | DnaJ heat shock protein family (Hsp40) member B1 | | | | 2.154 |
| DNAJB5 | DnaJ heat shock protein family (Hsp40) member B5 | | 2.591 | 6.794 | 13.824 |
| DNAJB9 | DnaJ heat shock protein family (Hsp40) member B9 | | | | 2.41 |
| DNAJC5 | DnaJ heat shock protein family (Hsp40) member C5 | | | | 2.094 |
| EIF2AK3 | eukaryotic translation initiation factor 2 alpha kinase 3 | Activates a signaling cascade resulting in an overall reduction in protein synthesis | | | 2.07 |
| FOSL1 | FOS like 1, AP-1 transcription factor subunit | FOS proteins are cell proliferation and differentiation regulators | | 2.707 | 3.519 |
| FTH1 | ferritin heavy chain 1 | These genes encode subunits of ferritin, a major protein for intracellular storage of iron ions | | | 2.11 |
| FTL | ferritin light chain | | | 2.601 | 4.68 |
| GSK3B | glycogen synthase kinase 3 beta | Might be involved in Nrf2 degradation | | | 2.485 |
| GSTO1 | glutathione S-transferase omega 1 | Antioxidant activity | | | 2.246 |
| HERPUD1 | homocysteine inducible ER protein with ubiquitin like domain 1 | Plays a role in protein degradation | | | 2.252 |
| HMOX1 | heme oxygenase 1 | Plays an essential role in heme catabolism | | 2.111 | 3.87 |
| HSPB8 | heat shock protein family B (small) member 8 | Contributes to the proteolytic degradation of proteins with folding defects | | 2.062 | 2.57 |
| IRS2 | insulin receptor substrate 2 | Transmits mitogenic and anti-apoptotic signals from the insulin receptor | | | 2 |
| MAF | MAF bZIP transcription factor | Down-regulates detoxification enzyme gene expression by dimerizing with MAFG. Prevents dimerization of MAFG and NRF2 | −2.411 | −3.486 | −5.825 |
| MAFG | MAF bZIP transcription factor G | Dimerizes with Nrf2 facilitating its attachment to antioxidant response elements present in the promoter region of Nrf2-regulated genes | | 3.199 | 4.374 |
| MAP3K5 | mitogen-activated protein kinase 5 | Involved in the oxidative stress response | | | −2.106 |
| MAPK8 | mitogen-activated protein kinase 8 | Encodes the JNK1 protein. Nrf2 is transported to the nucleus under the control of the ERK and JNK signaling pathways | | 2.048 | 3.23 |

-continued

| GENES | | | Expression with respect to the nontreated control or to the solvent control | | |
|---|---|---|---|---|---|
| Symbol | English name | Function of the protein encoded by the gene | Marjolaine | Ess. O Immortelle | Marjolaine and Ess. O Immortelle |
| MAPK14 | mitogen-activated protein kinase 14 | Signaling pathway involved in proliferation and differentiation | | 2.565 | 2.649 |
| NQO2 | N-ribosyldihydronicotinamide: quinone reductase 2 | Detoxification enzyme induced by Nrf2 activation | | 2.201 | 2.709 |
| PIK3C2B | phosphatidylinositol-4-phosphate 3-kinase catalytic subunit type 2 beta | Plays a role in cell proliferation, survival and migration, and also intracellular protein transport | | −2.318 | −2.486 |
| PIK3C2G | phosphatidylinositol-4-phosphate 3-kinase catalytic subunit type 2 gamma | | −4.325 | −6.072 | −17.725 |
| PRKCD | protein kinase C delta | Promotes Nrf2 translocation to the nucleus | | | 3.192 |
| PRKCH | protein kinase C eta | | | | 2.617 |
| PRKCI | protein kinase C iota | | | | 2.064 |
| RRAS2 | related RAS viral (r-ras) oncogene homolog 2 | Might activate signaling pathways controlling normal cell growth and also differentiation | | 2.67 | 3.206 |
| SQSTM1 | sequestosome 1 | Is part of the p62/SQSTM1 complex, this complex is activated by Nrf2. p62 sequesters Klf1 for autophagic degradation, thus enabling Nrf2 stabilization | | | 2.364 |
| TXNIP | thioredoxin interacting protein | Inhibits the antioxidant function of thioredoxin resulting in an accumulation of oxidative oxygen species | | −3.765 | −3.875 |
| TXNRD1 | thioredoxin reductase 1 | Protects cells against oxidative stress and is induced by Nrf2 | | 5.323 | 7.679 |

The Z-score of the NRF-2 pathway for antioxidant defense in response to the treatment of the skin explants with the marjolaine extract, the essential oil of Immortelle and a combination thereof was calculated by the software used and is indicated in table 2 below.

TABLE 2

| | Marjolaine extract | Essential oil (Ess. O) of Immortelle | Marjolaine extract and Ess. O of Immortelle |
|---|---|---|---|
| NRF-2 pathway | −1 | 1.069 | 2.449 |

From this table, it emerges that the marjolaine extract, used alone, has a tendency to inhibit the NRF-2 pathway, contrary to the essential oil of Immortelle. However, these effects are not significant. On the other hand, it appears that the combination of the two extracts result in a clear activation of the NRF-2 pathway, thereby demonstrating the synergistic effect of these two extracts.

2b) Epidermal Differentiation: Increase in the Barrier Function

Table 3 below presents the difference in expression of the genes that are involved in epidermal differentiation following the treatment of the skin explants with the marjolaine extract, the essential oil of Immortelle and a combination thereof.

| GENES | | | Expression with respect to the nontreated control or the solvent control | | |
|---|---|---|---|---|---|
| Symbol | English name | Function of the protein encoded by the gene | Marjolaine | Ess. O Immortelle | Marjolaine and Ess. O Immortelle |
| ABCA12 | ATP binding cassette subfamily A member 12 | Involved in cholesterol transport in the skin and is involved in maintaining the epidermal barrier to lipids | 2.018 | 2.427 | 3.398 |
| ALOXE3 | arachidonate lipoxygenase 3 | Involved in a metabolic pathway essential for maintaining the barrier function of the skin | | | 2.263 |
| ANXA1 | annexin A1 | Localization of this protein in tonofilament-enriched keratinocytes. Plays a role in the formation of the keratinocyte cytoskeleton. | | 2.634 | 4.958 |
| CAMP | cathelicidin antimicrobial peptide | Plays an essential role in the immune defense of the skin against bacterial infections | 4.17 | | 4.291 |
| CDH1 | cadherin 1 | Belongs to the family of epithelial cadherins which are calcium-dependent adhesion proteins which form intercellular junctions. CDH1 is only functionally active in differentiated keratinocytes forming organized intercellular junctions. | | | 2.019 |
| CERS3 | ceramide synthase 3 | Synthesizes certain skin ceramides. Maintains the barrier function | | | 2.007 |
| CNFN | cornifelin | Cornified envelope constituent | 4.441 | | 8.02 |
| CYP27B1 | cytochrome P450 family 27 subfamily B member 1 | Plays an important role in vitamin D metabolism and the maintaining of calcium homeostasis and epidermal differentiation | 2.361 | 3.835 | 4.071 |

-continued

| GENES | | | Expression with respect to the nontreated control or the solvent control | | |
|---|---|---|---|---|---|
| Symbol | English name | Function of the protein encoded by the gene | Marjolaine | Ess. O Immortelle | Marjolaine and Ess. O Immortelle |
| DEFB4A/ DEFB4B | defensin beta 4A | Antimicrobial peptide which contributes to the immune defense of the skin | 13.089 | | 15.134 |
| DSG3 | desmoglein 3 | Calcium-dependent transmembrane glycoprotein which binds to the other proteins that make up desmosomes. It is mainly expressed in the basal part of the epidermis | | 2.938 | 6.183 |
| EGF | epidermal growth factor | Growth factor which stimulates keratinocyte proliferation and differentiation | | 2.638 | |
| ELF3 | E74 like ETS transcription factor 3 | Transcription factor involved in epidermal differentiation | 4.481 | 4.632 | 17.117 |
| ELOVL4 | ELOVL fatty acid elongase 4 | Participates in epidermal ceramide synthesis by catalyzing the first reaction of the long-chain fatty acid extension cycle | 2.761 | 3.134 | 7.512 |
| EPHA2 | EPH receptor A2 | Tyrosine kinase receptor which triggers keratinocyte differentiation | 2.356 | 3.81 | 3.63 |
| EREG | epiregulin | Member of the epidermal growth factor (EGF) family. Growth factor which regulates keratinocyte proliferation and differentiation | 2.166 | 2.129 | 6.381 |
| ERRFI1 | ERBB receptor feedback inhibitor 1 | Epidermal differentiation regulator, contributes to maintaining the epidermal barrier | | | 2.155 |
| FABP5 | fatty acid binding protein 5 | Induces keratinocyte differentiation by increasing the transcriptional activity of peroxisome (PPAR)-activated receptors by transporting fatty acids directly to PPARs | | | 2.182 |
| FLG | filaggrin | Filaggrin (synthesized in the form of a precursor, profilaggrin) is a protein, the role of which is to aggregate keratin intermediate filaments during cornified envelope formation | −2.633 | | |
| FGF7 | fibroblast growth factor 7 | Epithelial cell-specific growth factor (also known as KGF for "Keratinocyte Growth Factor"), the mitogenic activity of which is mainly demonstrated in keratinocytes | | 2.078 | |
| GRHL1 | grainyhead like transcription factor 1 | Transcription factor involved in epithelial development. Epidermal differentiation regulator, contributes to maintaining the epidermal barrier | | | 2.651 |
| GRHL2 | grainyhead like transcription factor 1 | Inhibits keratinocyte differentiation via epigenetic mechanisms | | −2.393 | −3.865 |
| GRHL3 | grainyhead like transcription factor 3 | Protein essential for epidermal barrier formation | 2.149 | 2.888 | 8.2 |
| HBP1 | HMG-box transcription factor 1 | Involved in keratinocyte differentiation | | | 2.066 |
| HGF | hepatocyte growth factor | Growth factor regulating cell growth, cell motility and morphogenesis. Its stimulates mitosis in particular during tissue regeneration | | | 3.197 |
| HOXA7 | homeobox A7 | Suppresses expression of differentiation-regulating genes during keratinocyte proliferation | | | −2.423 |
| ITGB1 | integrin subunit beta 1 | Adhesion protein of basal keratinocytes at the epidermal junction. Hemidesmosome component | | | 2.067 |
| JUP | junction plakoglobin | Major cytoplasmic component of desmosomes | | | 2.204 |
| KLF5 | Kruppel like factor 5 | Transcription factor which increases keratinocyte proliferation | | | 2.298 |
| KRT6B | Keratin 6B | Structural protein involved in epidermal keratinization | | | 2.455 |
| LATS2 | large tumor suppressor kinase 2 | Interacts with centrosome proteins, it is essential for mitosis initiation and is involved in keratinocyte differentiation | | | 2.411 |
| LCE3A | late cornified envelope 3A | Protein component of the cornified envelope | 9.888 | | 11.481 |
| LCE3C | late cornified envelope 3C | | 6.177 | | 8.285 |
| LCE3D | late cornified envelope 3D | | 4.761 | 2.136 | 8.197 |
| LCE3E | late cornified envelope 3E | | 5.068 | | 5.917 |
| LOR | loricrin | Major protein component of the cornified envelope | −2.097 | | |
| OVOL2 | ovo like zinc finger 2 | Regulates cell proliferation in the basal layer of the epidermis | −2.291 | | −2.853 |
| PLK1 | polo like kinase 1 | Strongly expressed during mitosis, it is required for cell proliferation | | −3.252 | −2.383 |
| PPARA | peroxisome proliferator activated receptor alpha | Regulates epidermal differentiation | | 2.077 | 2.779 |
| PPARD | peroxisome proliferator activated receptor delta | | | 2.764 | 4.155 | 8.966 |
| PRKCH | protein kinase C eta | Regulates keratinocyte differentiation | | | 2.617 |
| S100A7 | S100 calcium binding protein A7 | Protein components of the cornified envelope | 2.717 | | 3.22 |
| S100A11 | S100 calcium binding protein A11 | | | | 2.019 |
| SPRR1A | small proline rich protein 1A | Cornified envelope components | 4.665 | 5.288 | 16.546 |

-continued

| GENES | | | Expression with respect to the nontreated control or the solvent control | | |
|---|---|---|---|---|---|
| Symbol | English name | Function of the protein encoded by the gene | Marjolaine | Ess. O Immortelle | Marjolaine and Ess. O Immortelle |
| SPRR1B | small proline rich protein 1B | | 2.544 | 3.095 | 4.893 |
| TGM1 | transglutaminase 1 | Involved in cornified envelope formation by creating bridges between the proteins forming said envelope | 4.557 | 3.819 | 8.105 |
| TGM3 | transglutaminase 3 | | | | 6.104 |
| TP63 | tumor protein p63 | Transcription factor involved in skin development which inhibits epidermal differentiation | | −3.148 | −7.121 |
| WNT16 | Wnt family member 16 | WNT16B expression increases the amount of proliferating cells and prolongs primary keratinocyte clonogenicity | −2.096 | −10.838 | −17.812 |
| ZFP36 | ZFP36 ring finger protein | Influences keratinocyte differentiation | | | 2.527 |

This table shows that certain genes involved in keratinocyte differentiation are upregulated and others which inhibit keratinocyte differentiation are downregulated. Furthermore, genes of growth factors (HGF, epiregulin) are also upregulated, allowing the reserve of proliferating keratinocytes to be maintained. All of these genes will enable a reinforcement of the epidermal barrier.

3) Conclusion

This example demonstrates, by means of an ex-vivo transcriptome analysis using DNA chips, that the composition of the invention makes it possible to stimulate the genes involved in particular in renewal of the epidermis and oxidative stress management, thus making it possible to combat aging of the skin due in particular to exterior attacks generating oxidative stress, and to reinforce the barrier function of the skin.

Example 2: Cosmetic Composition

The following composition is prepared in a manner that is conventional for those skilled in the art, by mixing the ingredients below in the weight proportions indicated.

| | |
|---|---|
| Essential oil of Immortelle | 0.01-0.1% |
| Extract of marjolaine leaves | 0.2-0.8% |
| Adenosine | 0.05% |
| Oils | 5-15% |
| Oily gelling agents | 1-5% |
| Aqueous gelling agents | 1-3% |
| Polyols | 20-25% |
| Sequestering agent | qs |
| Antioxidants | qs |

-continued

| | |
|---|---|
| Fragrance | qs |
| Preserving agents | qs |
| Water | qs 100% |

The invention claimed is:

1. A cosmetic composition comprising the following plant extracts:
   an essential oil of Immortelle, which is the product of hydrodistillation of the flowers or flowering heads of *Helichrysum italicum*, in an amount from 0.001 to 0.1 wt % relative to the total weight of the composition,
   a terpene extract, which is obtained by extraction with a protic polar solvent of the aerial parts of *Origanum majorana* selected from the stem, the leaves and mixtures thereof, wherein the solvent is selected from the group consisting of water, a monoalcohol, a glycol, a polyol and mixtures thereof, in an amount of from 0.001 to 5 wt % relative to the total weight of the composition, and
   a physiologically acceptable medium comprising an aqueous phase comprising water and a polyol,
   wherein the combination of said plant extracts synergistically activates the expression of the genes involved in the defense of the skin against oxidation phenomena, and of the genes involved in the regulation of epidermal differentiation.

2. A cosmetic process for combating the signs of skin aging, in particular the formation of wrinkles, the slackening of the skin and the loss of radiance of the complexion, caused in particular by exposure to UV radiation and/or to blue light, to smoking and/or to pollution, and/or for combating dryness of the skin, comprising the topical application of the composition as claimed in claim 1 to the skin.

* * * * *